United States Patent [19]

Walton

[11] Patent Number: 4,668,633
[45] Date of Patent: May 26, 1987

[54] GROWTH CONTAINER AND METHOD FOR PATHOGENIC AND OTHER LABORATORY ORGANISMS

[76] Inventor: John R. Walton, 2558 Seahorse Ave., Ventura, Calif. 93001

[21] Appl. No.: 717,304

[22] Filed: Mar. 28, 1985

[51] Int. Cl.⁴ .............................................. C12M 1/22
[52] U.S. Cl. .................................... 435/298; 435/292; 435/301
[58] Field of Search .............................. 435/292–294, 435/297–301, 29, 30; 220/46, 306; 215/6, 307, 321, DIG. 1; 206/204

[56] References Cited

U.S. PATENT DOCUMENTS

| | | | |
|---|---|---|---|
| 2,144,255 | 1/1939 | Carpenter | 435/297 |
| 2,348,448 | 5/1944 | Brewer | 195/139 |
| 3,158,553 | 11/1964 | Carski | 215/307 |
| 3,165,450 | 1/1965 | Scheidt | 435/298 |
| 3,388,043 | 6/1968 | Ingvorsen | 435/294 |
| 3,632,478 | 1/1972 | Fink | 435/297 |
| 3,769,936 | 11/1973 | Swanson et al. | 119/15 |
| 4,160,700 | 7/1979 | Boomus et al. | 435/298 |
| 4,294,924 | 10/1981 | Pepicelli et al. | 435/30 |
| 4,299,921 | 11/1981 | Youssef | 435/298 |
| 4,301,252 | 11/1981 | Baker et al. | 435/298 |

FOREIGN PATENT DOCUMENTS

| | | | |
|---|---|---|---|
| 56473 | 6/1967 | Fed. Rep. of Germany | 220/306 |
| 387795 | 2/1933 | United Kingdom | 435/298 |
| 2098968 | 12/1982 | United Kingdom | 220/306 |

*Primary Examiner*—Samuel Scott
*Assistant Examiner*—Noah Kamen
*Attorney, Agent, or Firm*—Koppel & Harris

[57] ABSTRACT

A growth container for laboratory organisms such as fungi, TB bacilli, yeast, virus or bacteria in which a well for the growth medium is spaced inwardly from an outer and higher wall. A lid snaps in place over the dish to substantially enclose the growth medium. An absorbent material, preferably a ring of filter paper, is placed in the space between the well and the outer dish wall to humidify the container when the material is wet, and to collect condensation from the lid which may include dangerous spores. Condensation is collected from a blocking ring on the underside of the lid by inversion of the dish and absorption onto a filter paper ring. An access opening in the lid permits material to be removed from or added to the growth medium with the lid only partially disengaged. The well may contain a single growth medium or a number of segregated growth compartments. A method of obtaining a slide specimen is described in which a slide member is placed over the well and the organism is grown until it adheres to the underside of the slide member. The organism is then severed and the slide member and adhered specimen removed from the container. Substantially undamaged specimens are thus obtained quickly and with safety.

2 Claims, 6 Drawing Figures

GROWTH CONTAINER AND METHOD FOR PATHOGENIC AND OTHER LABORATORY ORGANISMS

BACKGROUND OF THE INVENTION

1. Field of the Invention

This invention relates to growth containers such as petri dishes used to grow laboratory organisms, and more particularly to an improved growth container and method of growing and collecting specimens of pathogenic and other laboratory organisms.

2. Description of the Prior Art

Glass bottles have typically been used in the past for laboratory growth of fungi and similar microbiotic organisms. A cap is provided for the bottle, with the cap normally cracked slightly open to exchange the necessary gases for fungal growth. Glass bottles and caps are not permeable to gases, whereas styrene is permeable. This type of growth environment has several problems. First, it does not provide for the regulation of gases or moisture within the bottle. Excess moisture resulting from condensation within the bottle can collect on the growth medium, thereby selecting for a surplus of bacteria and preventing fungal growth. The excess moisture condenses on the interior wall of the bottle and flows back into the growth medium, diluting antibiotics in the primary selected media. Furthermore, when a sample is removed from the bottle it is often difficult to trace the exact location from which it was taken, thus making a complete analysis difficult. Another problem is that, when the media inside the bottle is too wet, it is more difficult to handle the bottle because the surface of the media tends to flow when the bottle is turned. On the other hand, if the cap is left open too far the interior of the bottle can become excessively dry. Also, it is necessary to take the cap off to remove a sample, creating a danger that harmful pathogenic spores will escape from the bottle.

Specimens are normally removed from the bottle by means of a wire loop at the end of a tube. The specimens are then mixed on a slide for viewing under a microscope, and in the mixing process the specimens are sometimes destroyed. In addition, it is difficult to clearly identify and mark the exact location of the fungus as it is growing because of the refraction of the glass bottle wall; typical marking pens do not adhere to glass.

Various petri dish containers have also been devised for growing microorganisms. In U.S. Pat. No. 4,294,924 to Pepicelli et al. a container for growing anaerobic microorganisms has a cone-shaped dish and a matching cone-shaped cover with an agar medium contained between the two. No air vents are provided, nor is there any positive moisture control within the container. U.S. Pat. No. 4,299,921 to Youssef discloses a petri dish with a filter gasket attached to the cover to prevent contamination from outside the dish. U.S. Pat. No. 4,160,700 to Boomus et al. discloses a petri dish and lid with mating annular walls, in which annular flanges are provided on the dish and lid to facilitate opening the enclosure with one hand. In U.S. Pat. No. 3,769,936 to Swanson et al. the cover for a simple petri dish is provided with a small orifice for introducing materials into the dish without removing the cover, with a tab or resilient strip normally covering the orifice. In U.S. Pat. No. 2,348,448 to Brewer a petri dish is provided with a cover having a center recess in its lower surface to provide a space for organism growth. Placement of the cover over a growth medium in the dish provides an anaerobic environment.

While each of the above dish devices appear to provide useful growth environments, none of them provide for moisture regulation to prevent either an excessive build-up of moisture or an excessively dry environment, none of them provide a mechanism for mounting a specimen on a slide without the danger of destroying the specimen, and except for U.S. Pat. No. 3,769,936 none of them have the capability of accessing the interior of the container without removing the cover.

SUMMARY OF THE INVENTION

In view of the above problems associated with the prior art, it is the object of this invention to provide a growth container and method of growing pathogenic and other laboratory organisms which includes a moisture control mechanism to prevent the interior of the container from becoming either too wet or too dry; which is safe to use with dangerous pathogenic organisms in that it inhibits contaminated condensation from reaching the periphery of the container; which does not have to be completely opened to remove samples and has a locking mechanism to prevent accidental opening; which enables direct growth of a microbiotic sample onto a slide and thereby eliminates the problem of organism destruction when transferring a sample from a growth medium to a slide; which provides an effective environment for rapid growth by permitting an exchange of atmospheric gases without comprising safety; which permits clear viewing of the organism being grown; and which permits several different organisms to be segregated and grown in the same container.

In the accomplishment of these and other objects of the invention, a growth container for pathogenic and other laboratory organisms is provided which includes a dish having a floor, an outer substantially closed wall extending upward from the floor, and an inner substantially closed wall spaced inward from the outer wall and extending upward from the floor to a height less than that of the outer wall. The inner wall forms a well for a growth medium, and a lid is adapted to fit over the outer wall to substantially close the container. The dish is adapted to accommodate a sufficient quantity of a liquid absorbent material in the space between the inner and outer walls to humidify the interior of the container when the absorbent material is wet and the container is closed.

Excessive condensation is collected by means of a blocking ring which depends from the lower surface of the lid over the liquid absorbent material. The ring blocks the outward flow of condensation along the lower lid surface so that an excess of condensation drips onto and is retained by the liquid absorbent material. In addition to protecting the growth medium from excessive moisture, this inhibits contaminated water from escaping from the container. The liquid absorbent material is preferably provided in the form of a paper filter ring which falls onto the lid when the container is inverted and absorbs moisture collected at the ring.

The container is adapted to accommodate a slide member placed over the top of the well. An organism growing within the well comes into contact with and adheres to the underside of the slide member, which can then be removed and examined under a microscope without damaging the adhered portion of the fungus.

The lid includes a downward depending side wall which fits over and forms a leaky mutual engagement with the outer dish wall, permitting a slight flow of gases between the interior and exterior of the container to provide the necessary atmosphere for microorganism growth. The lid side wall and the outer dish wall include mutually opposed snap rings or tabs, and at least one of the walls is formed from a stiffly flexible material so that the lid may be snapped into position over the dish. An access opening in the lid side wall permits access to the interior of the container with the lid only partially disengaged from the dish. The well may be subdivided into segregated growth areas.

These and other features and objects of the invention will be apparent to those skilled in the art from the following detailed description of preferred embodiment, together with the accompanying drawings, in which:

DETAILED DESCRIPTION OF PREFERRED EMBODIMENTS

Figure 1:
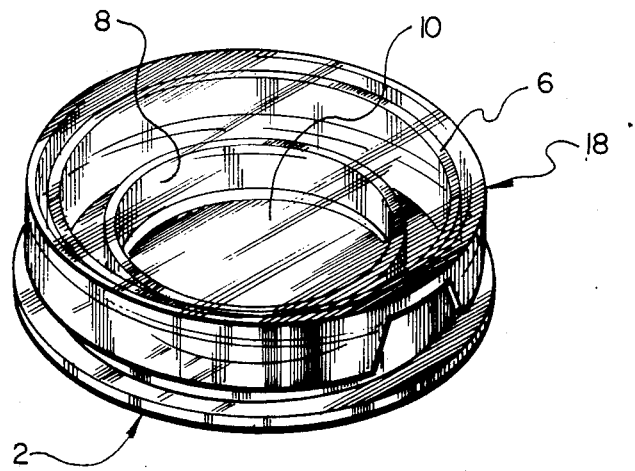
FIG. 1 is a perspective view of a laboratory organism growth container constructed in accordance with the invention.
Figure 2:
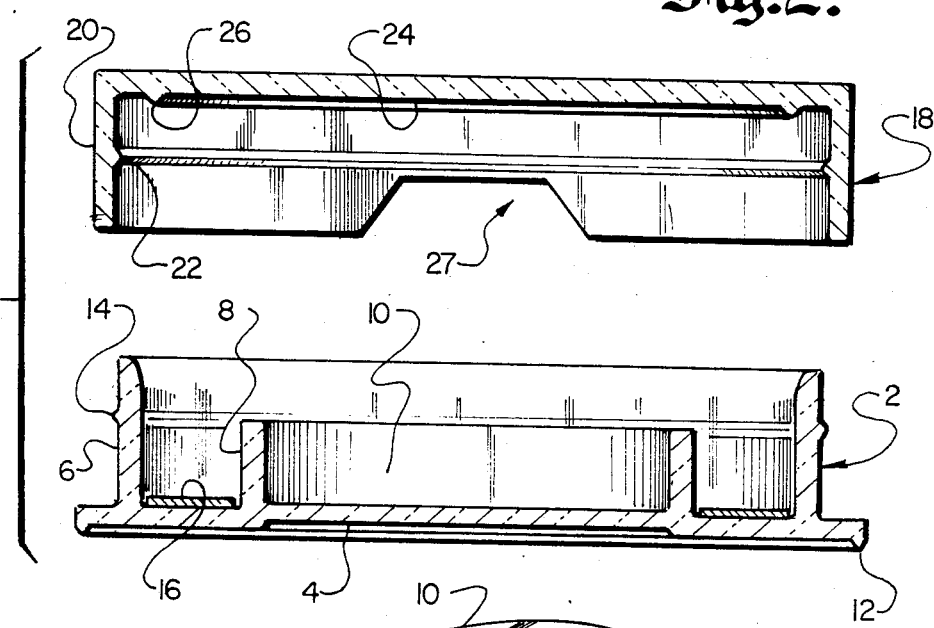
FIG. 2 is a sectional view of the growth container with the lid elevated over the dish.

The construction of a preferred embodiment of the growth container of the present invention is shown in FIGS. 1 and 2. The dimensions given herein for this embodiment are exemplary only, and may be adjusted as desired. A dish 2 which is designed to hold a growth medium and a laboratory organism being grown therein includes a lower circular floor 4, an outer annular wall 6 which extends generally upward from the floor near its periphery, and an inner annular wall 8 which extends upward from the floor at a location inward of outer wall 6. The container is preferably formed from a clear molded plastic material such as acrylic, styrene or polycarbonate, which allows its contents to be clearly viewed from the outside.

Inner wall 8 together with the portion of floor 4 which it encloses forms a well 10 designed to contain a microbiological organism and a growth medium or agar for the organism. Typical nominal dimensions for the dish would be an overall diameter of 2⅜", an outer wall inner diameter of 2¼", an inner wall inner diameter of 1½", an outer wall height ½" above the floor, a height differential between the inner and outer walls of 3/32", a well depth of ¼", and a plastic thickness of 1/16".

A downward depending lip 12 is formed around the outer lower periphery of the dish to facilitate stacking with other dishes. The inner surface of outer wall 6 is slightly tapered in its upper region to facilitate inward bending of the wall, and the wall material itself is stiffly flexible. An annular protuberance in the form of a locking ring 14 extends outward about 0.04" from outer wall 6 and slightly below the top of the wall.

A space of about 5/16" is left between the inner and outer walls. Into this space a liquid absorbent material such as a ring of filter paper 16 is placed. As described below, filter paper 16 is instrumental in regulating the moisture content of the growth medium, and also assists in preventing the escape of contaminated condensation from the container.

A circular lid 18 is provided to close the dish 2. Lid 18 is molded from the same material and to the same thickness as dish 2. An annular side wall 20 depends down from the outer circumference of the lid to a depth somewhat less than the height of the outer dish wall 6. An annular protuberance in the form of locking ring 22 extends inward about 0.004" around the inner periphery and just below the annular ring of base 2 about half way down the side on wall 6. The inner diameter of the lid side wall 20 is about equal to the outer diameter of the outer dish wall 6, such that the lid can be slid down over the dish with locking rings 14 and 22 engaging each other and forcing the lid side wall and outer dish wall apart as the lid continues moving downward. Lid snap ring 22 then snaps into place below dish snap ring 14 when the lid is pushed down all the way so that the lid ceiling 24 rests on top of the outer dish wall 6. In this position the lid is positively retained on the dish, and cannot be opened until sufficient pressure is applied to overcome the snap ring resistance. The surfaces of snap rings 14 and 18 are not perfectly smooth, and permit a slight flow of gas between the inside and outside of the container when the lid is in place. This, plus the permeability of the chosen plastic, enables sufficient atmospheric gases to flow into and out of the container to sustain the growth of a fungus or bacterial organism within the well.

An annular bead 26 depends down from the lid ceiling at an inward location from the lid side wall such that it is vertically aligned over the filter paper 16 which surrounds the dish well. Bead 26, which is about 1/16" wide at its base and depends downward about 1/16", forms a blocking ring which prevents condensed moisture on the lid ceiling above the well from flowing outward to the periphery of the lid, and from there possibly escaping entirely from the container. This is particularly important in the case of pathogenic organisms such as many of the common TB and fungal pathogens, which are infective with very low exposures. Condensation which may contain the spores of such organisms collects at bead 26, and from there can drip down onto the underlying filter paper 16, which absorbs the moisture and prevents it from leaving the container. The width of the filter paper is slightly less than the distance between the inner and outer dish walls so that, before sufficient moisture has accumulated on bead 26 to drip on the filter paper, the container can be inverted so that the filter paper falls onto the bead and absorbs the moisture in its vicinity. The container is then inverted again, allowing the ring of filter paper to fall back into the space surrounding well 10. The use of removable filter paper makes it very easy to remove the filter after it has been used and to replace it with another piece. However, a thicker material such as a cotton wadding could also be used, and the absorbent material could be adhered to the dish within the space between the inner and outer walls rather than being readily removable.

In addition to preventing infected condensation from escaping from the container, the filter paper limits excessive moisture within the container, whether or not infected. Excessive moisture within the growth medium can destroy the organism being grown. By collecting and trapping excessive moisture with the filter paper, this danger is removed.

The filter paper also plays an important moisture control function when the problem is excessive drying of the medium as opposed to excessive moisture. The humidity within the container must be kept above a minimum level to prevent the agar from drying and shrinking in well 10, and at higher than minimum levels to promote rapid growth. By wetting the filter paper before the lid is placed over the dish, preferably with a few drops of filtered water, the interior of the container can be effectively humidified for long periods of time to promote rapid growth levels.

The described container is particularly useful with Fungi Imperfecti, which is the classification by which medically important fungi are known. This group has the ability to produce spores by two methods. The first and simplest of the methods involves the breaking up of sections of the vegetative or "feeding" mycelia into small units or seeds known as arthrospores. This type typically produces a wet colony like yeast and has no aerial hyphae or reproductive mycelia borne off the agar surface in the well. The second and most prevalent type produces bunches of spores or fruit-bearing heads, called conidiophores, which are borne on aerial hyphae off the agar surface. This produces the characteristic fuzzy mold look normally associated with a fungus.

One of the most important advantages of the described container is the safety which it provides for handling medically hazardous, slow growing fungi and acid-fast bacilli (better known as TB or tuberculin bacilli). The snap rings on the lid and dish prevent the lid from accidentally coming off and releasing infective agents, as well as providing a leaky interface so that atmospheric gases can exchange within the dish. The isolation of the inner media well from the outer wall, as well as the provision of the blocking ring on the lid and the liquid absorbent material surrounding the well, are all safety features, serving to prevent aerial spores and moisture contaminated by bacilli or arthrospores from escaping the interior of the container. Another advantage of the container is the ability to view the colony from both its growth surface and the underside undistorted by moisture and the irregularities and curvatures associated with glass containers. The collection of excess moisture and the maintenance of a proper humidity level by means of the filter paper ring surrounding the growth well improve the recovery rate of significant organisms, reduce recovery time, extend media life beyond conventional containers and substantially eliminate the dilution of the selective antibiotics which occurs with agar media stored in glass bottles.

Figure 3:
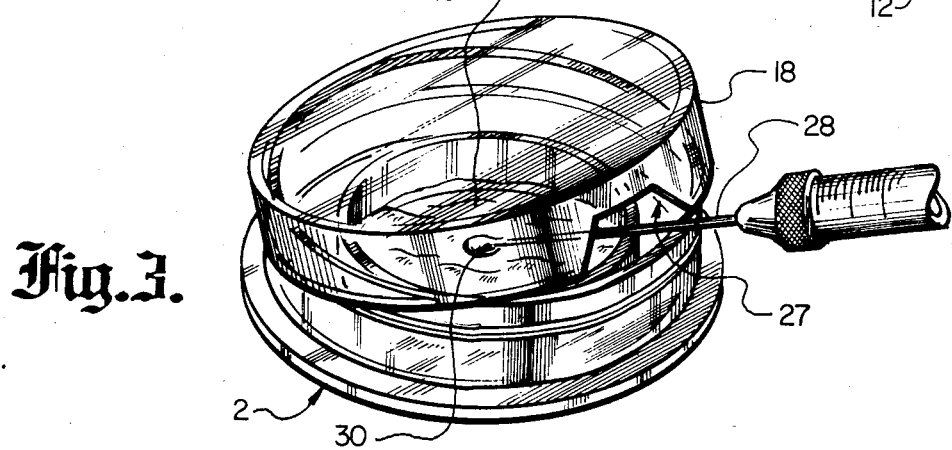
FIG. 3 is a perspective view of the growth container illustrating how its interior may be accessed without completely removing its lid.

Referring back to FIG. 2, another feature involves the provision of an access opening 27 which extends upward from the bottom of lid side wall 20 about half way to the lid ceiling. For the previous lid dimensions given, the bottom of the opening is preferably about ¾" wide at the bottom tapering to ½", and the opening is about 5/32" deep. This access opening is used for removing a specimen from the growth medium or adding material thereto, as illustrated in FIG. 3. Only the portion of the lid which includes access opening 27 is lifted up from the dish, and then only far enough to permit a tube 28 with a loop 30 at its end to be inserted through the access opening and into the growth medium. In this manner specimens can be obtained or material added to the growth medium while the container is still mostly closed. There is little danger of the user being infected from spores within the container, especially since any moisture collected on the lid moisture blocking ring will tend to flow away from the access portion of the lid when it is lifted.

Slide culturing is the most effective method for safely identifying fungal organisms. Medically important fungi are identified by spore type and configuration and separated from the many water and airborne mold contaminants that plague the laboratory technologist. Airborne molds such as penicillium are a particular problem. Prior to the present invention a common method of slide culturing involved cutting out an agar square with the appropriate growth, placing it on a microscope slide, covering it with a coverslip, placing this combination in another empty culture dish, and then humidifying, reculturing, separating, staining and viewing the specimen. An alternate and quicker method which is commonly used but quite dangerous, necessitating the use of a HEPA hood and gloves to protect the technologist (although the hood is usually a source of contamination as a result), is to simply scrape some fungus off the agar surface and smear the sample onto a glass slide for staining. This technique can spread aerial spores and TB bacilli throughout the work place. Although it is a quick and easy way to obtain a sample, it damages the sample and a considerable amount of time is normally wasted under the microscope trying to locate undamaged structures from which the organism can be identified.

Figure 4:
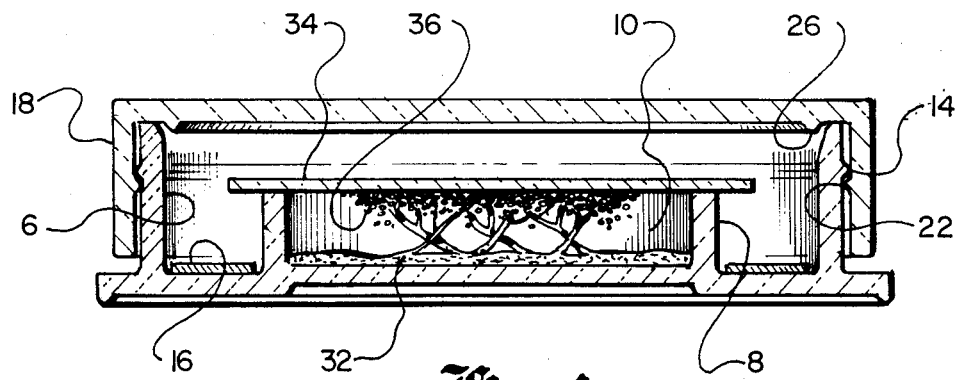
FIG. 4 is an enhanced sectional view of the growth container showing a fungus sample being grown onto a slide coverslip.

In accordance with the present invention, a technique has been developed which bypasses these problems and permits live cultures to be obtained quickly, easily, safely and without manipulating the organism on the agar surface, thereby obtaining perfect or near perfect organism structures. This technique and the accompanying container structure is shown in FIG. 4. An agar 32 substantially fills the well of the dish previously described to a level marginally below the upper end of the well wall 8, and a patient sample is inoculated onto the agar surface. A slide coverslip 34, preferably fairly large in the order of 1mm, thick and 22×40 mm. surface dimensions, is placed over the well. The coverslip can be positioned either with its opposite ends extending beyond the well on opposite sides, as illustrated in FIG. 4, or one end of the coverslip can be stuck into the edge of the agar medium itself and the other end rested on the opposing side of the well wall. When sufficient growth has occurred, the fungi or bacilli 36 will touch the underside of the coverslip surface by expanding aerially or by convex expansion. In either case a specimen of the organism will adhere to the underside of the coverslip. The coverslip is then removed by means of forceps, causing the organism to be severed between the agar and the coverslip but leaving an undamaged specimen adhered to its underside. The coverslip is then slid out through the lid access opening and placed with the specimen side down on a suitable microscope slide containing a drop of stain. Typically, lactophenol cotton blue would be used for fungi, iodine for yeast, and acid-fast stain for bacilli. Positive identification of the specimen can than be made microscopically.

Figure 5:
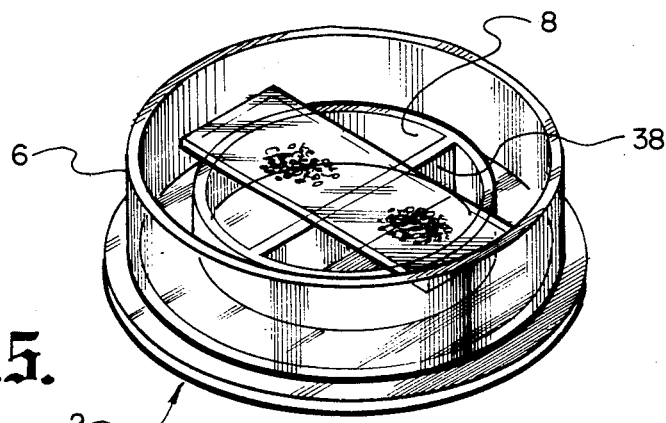
FIG. 5 is a perspective view of the dish portion of an embodiment of the growth container with two growth compartments.

Another embodiment of the invention is shown in FIG. 5. In this embodiment essentially the same dish 2 is employed as before, but the well formed by inner wall 8 is divided into two halves by means of a central divider wall 38 which extends diametrically across the well to a height equal to the well wall. With this dish two segregated growth media can be sustained on opposite sides of the divider wall at the same time. This is an important cost savings, since petri dishes are used in large quantities and this embodiment in effect provides two growth containers for little more than the price of one. It also permits two specimens to be obtained on a single slide.

Figure 6:
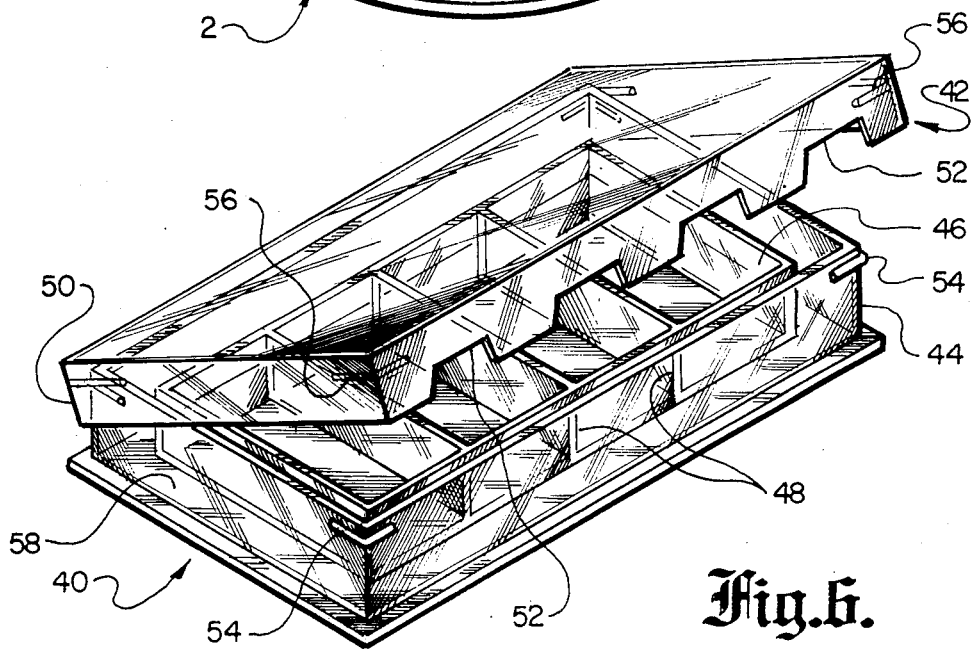
FIG. 6 is a perspective view of another embodiment of the growth container with more than two growth compartments.

Still greater savings are achieved with the rectangular embodiment of the invention shown in FIG. 6. In concept this container is similar to the circular containers previously described, but a rectangular dish 40 and lid 42 are used. The dish includes an outer wall 44 and an inwardly spaced inner wall 46, with three dividers walls 48 dividing the area within inner wall 46 into four segregated growth wells. Lid 42 has a depending peripheral side wall 50 into which four access openings 52 are formed in registration with each of the four growth wells or compartments in the dish. Instead of annular snap rings as in the previous embodiments, snap tabs 54 are located at each corner of outer wall 44 in registration with corresponding snap tabs 56 which extend inwardly from each of the corners of the lid wall 50. A ring of filter paper 58 may or may not be placed in the space between the inner and outer dish walls, depending upon the growth media and specimen types. Slide or coverslip cultures are still possible with this embodiment, as is the use of the access openings for obtaining samples from each of the different culture compartments.

While the inner wall is shown divided into four growth compartments, any convenient number of compartments may be formed. Rectangular dishes have the advantage of being easier to register on the sled used for filling them, whereas round dishes must be positioned by hand or by elaborate equipment in order to accurately fill two or more wells simultaneously. With rectangular dishes three or four different media can be dispensed simultaneously and with great reproducibility.

In application, the circular container with one growth well shown in FIGS. 1-4 would typically be used for primary cultures of a single sample of a fungus, TB bacillus, yeast or virus. The dual sample circular container shown in FIG. 5 would typically be used for primary, differential or selective media to grow fungi, TB bacillus, yeast or various aerobic or anaerobic bacteria. A rectangular container with three growth compartments would typically be used for differential or selective media, while the four compartment container shown in FIG. 6 would typically be used for differential or selective media, or for sensitivity studies of TB drugs.

Various embodiments of a novel and improved growth container for pathogenic and other laboratory organisms, and an associated method, have thus been shown and described. As numerous modifications and variations will occur to those skilled in the art, it is intended that the invention be limited only in terms of the appended claims.

I claim:

1. A growth container for pathogenic and other laboratory organisms, comprising:
 a dish having a floor, an outer substantially closed wall extending upward from the floor, and an inner substantially closed wall spaced inward from the outer wall and extending upward from the floor to a height less than that of the outer wall, the inner wall and subtended floor forming a well for a growth medium,
 a lid adapted to fit over the outer wall of the dish to substantially close the container,
 a blocking ring depending from the lower surface of the lid over the space between the inner and outer dish walls, the ring blocking and accumulating the outward flow of condensation along the lower lid surface so that an excess of condensation drips into the space between the inner and outer dish walls, and
 a sufficient quantity of a liquid absorbent material in the space between the inner and outer walls to humidify the interior of the container when the absorbent material is wet and the container is closed, and to prevent condensation dripped from the blocking ring from re-entering the growth medium well, whereby the growth medium is protected from both insufficient and excess moisture, the liquid absorbent material comprising a vertically movable absorbent filter ring disposed in the space between the inner and outer dish walls, the filter adapted to move through the container to contact and absorb moisture from the blocking ring when the container is inverted, and to return to its original position when the container is returned to an upright position.

2. A method of growing a pathogenic organism which is subject to excess condensation when grown in an enclosed petri dish, comprising the steps of:
 placing a growth medium for the organism in a well,
 substantially surrounding the well with a liquid absorbent material comprising a filter ring which is vertically movable within the enclosure,
 substantially enclosing the well and liquid absorbent material with a lid that is spaced above the well,
 collecting outward flowing condensation on the lower side of the lid along a locus which is vertically aligned with the liquid absorbent material,
 inverting the enclosure so that the filter ring falls to the lid and absorbs condensation along the locus,
 again inverting the enclosure to return the filter ring to its original position, and
 retaining excess collected condensation dripped onto the filter ring in the filter material to prevent it from re-entering the growth medium.

* * * * *